United States Patent
Bondzio

(10) Patent No.: US 9,518,922 B2
(45) Date of Patent: Dec. 13, 2016

(54) ARRANGEMENT FOR IN SITU MEASUREMENT OF AT LEAST THE OXYGEN CONTENT WITHIN A SOLIDS HEAP

(75) Inventor: Lars Bondzio, Groß-Umstadt (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 241 days.

(21) Appl. No.: 14/235,846

(22) PCT Filed: Aug. 1, 2011

(86) PCT No.: PCT/EP2011/063235
§ 371 (c)(1),
(2), (4) Date: Jan. 29, 2014

(87) PCT Pub. No.: WO2013/017162
PCT Pub. Date: Feb. 7, 2013

(65) Prior Publication Data
US 2014/0190826 A1  Jul. 10, 2014

(51) Int. Cl.
G01N 27/26 (2006.01)
G01N 21/64 (2006.01)
G01N 33/00 (2006.01)

(52) U.S. Cl.
CPC ............ *G01N 21/643* (2013.01); *G01N 27/26* (2013.01); *G01N 33/0075* (2013.01)

(58) Field of Classification Search
CPC ........... C22B 3/18; C22B 3/20; G01N 21/643; B62M 6/85
See application file for complete search history.

(56) References Cited

U.S. PATENT DOCUMENTS

| 2,913,386 | A | * | 11/1959 | Clark |
| 7,906,304 | B2 | * | 3/2011 | Kohr .................. C12M 21/04 435/166 |
| 2004/0175819 | A1 | * | 9/2004 | Kanitz ..................... B09B 1/00 435/262 |
| 2005/0211019 | A1 | * | 9/2005 | Crundwell et al. |
| 2008/0045349 | A1 | * | 2/2008 | Dobbins et al. .............. 473/131 |

(Continued)

FOREIGN PATENT DOCUMENTS

| CN | 1351673 A | 5/2002 |
| CN | 101341264 A | 1/2009 |

(Continued)

OTHER PUBLICATIONS

Ramamoorthy et al. (Journal or Material Science 38, 2003, 4271-7282).*

(Continued)

*Primary Examiner* — Jennifer Dieterle
(74) *Attorney, Agent, or Firm* — Christopher R. Powers; PatServe

(57) ABSTRACT

An arrangement for in situ measurement of at least one oxygen partial pressure within a solids heap, including: at least one measuring transducer arranged within the solids heap for locally registering oxygen partial pressure, wherein each measuring transducer is embodied to output a measurement signal representing oxygen partial pressure to a superordinated unit, which is arranged outside the solids heap and is embodied to receive and to process the measurement signals of each measuring transducer.

11 Claims, 1 Drawing Sheet

(56) References Cited

U.S. PATENT DOCUMENTS

2008/0173133 A1 7/2008 Rorke

FOREIGN PATENT DOCUMENTS

| CN | 102020252 A | 4/2011 |
|---|---|---|
| WO | 0071763 A1 | 11/2000 |
| WO | 0118263 A1 | 3/2001 |
| WO | 2004027099 A1 | 4/2004 |
| WO | 2004072636 A1 | 8/2004 |
| WO | 2013017162 A1 | 2/2013 |

OTHER PUBLICATIONS

Oxymax Cos 61 manual (pub Jun. 2005).*
Rayner, et al., Petroleum-hydrocarbon contamination and remediation by microbioventing at sub-Antarctic Macquarie Island, Cold Regions Science and Technology, Mar. 30, 2007, pp. 139-153, vol. 48, No. 2, XP022006316, ISSN: 0165-232X: DOI: 10.1016/J.COLDREGIONS.2006.11.001, Elsevier B.V., Amsterdam, The Netherlands.
Lizama, Hector M., Copper bioleaching behaviour in an aerated heap, International Journal of Mineral Processing, Jan. 1, 2001, pp. 257-269, vol. 62, Chapter 2.1 and 2.2, XP002354277, ISSN: 0301-7516, D0I: 10.1016/S0301-7516(00)00057-0, Elsevier Science Publishers, Amsterdam, The Netherlands.
May 23, 2012 International Search Report, EPO, The Netherlands.
Feb. 13, 2014 English Translation of IPR, WIPO, Geneva, Switzerland.

* cited by examiner

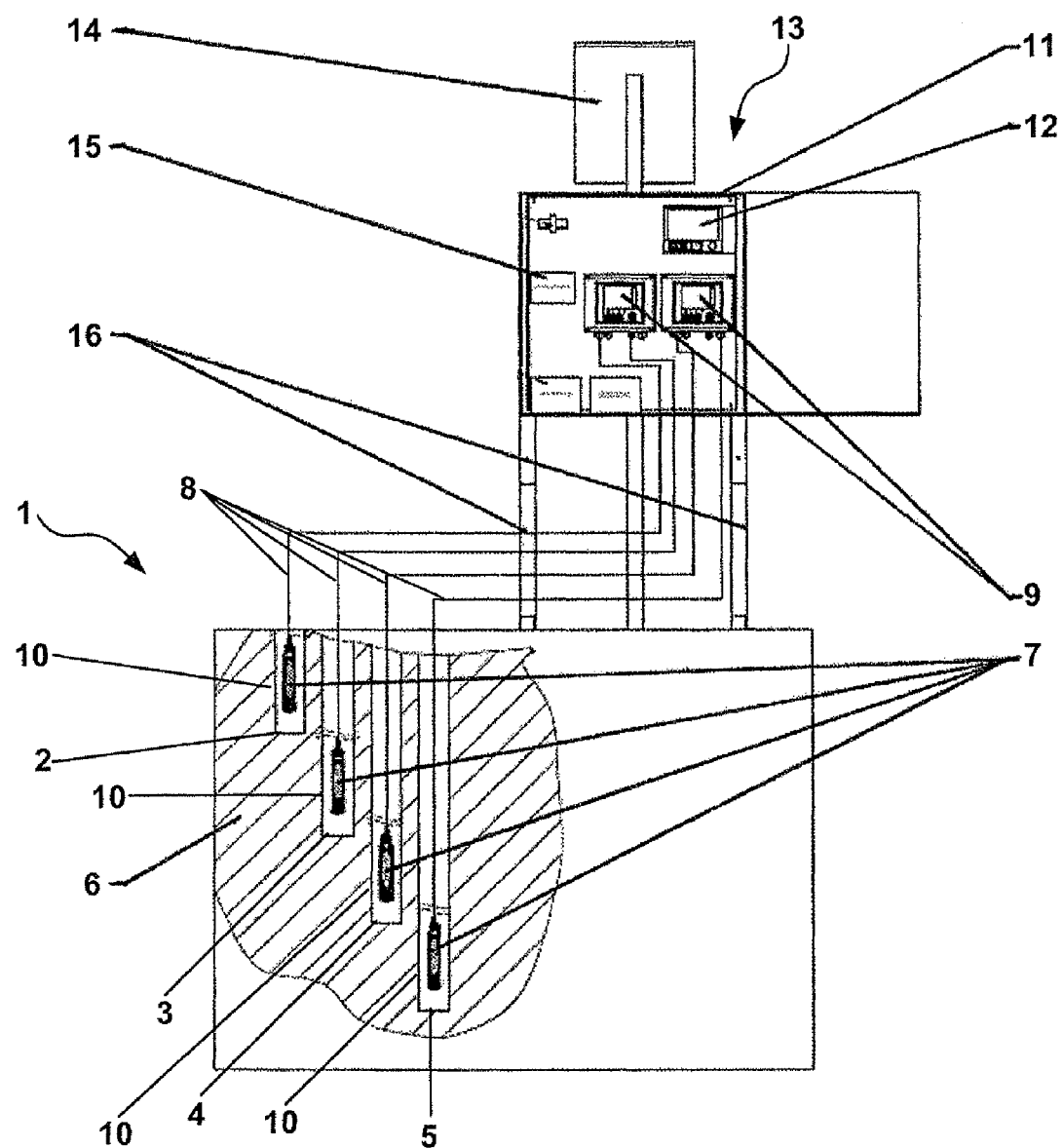

ARRANGEMENT FOR IN SITU MEASUREMENT OF AT LEAST THE OXYGEN CONTENT WITHIN A SOLIDS HEAP

TECHNICAL FIELD

The invention relates to an arrangement for in situ measurement of at least the oxygen content within a solids heap.

BACKGROUND DISCUSSION

In mining, however, also in waste processing, for example, in the case of composting or in the case of decontamination treatments of the most varied of materials, a series of processes, especially chemical, biological processes, are performed using solids heaps. For example, in the treatment of the most varied of ores, especially in the mining of copper and iron ores, always more frequently, microbiologically supported, leaching processes are being used. In the case of this microbial leaching, which is also referred to as "bio-leaching", microorganisms support the digestion of metal salts of insoluble ore minerals to water soluble salts. The terminology, microorganisms, refers, in the case of such processes, frequently to bacteria and archaea, which oxidize sulfide and elementary sulfur to sulfate and partially also divalent iron to trivalent iron. Examples of such bacteria include the sulfur bacteria, *Acidithiobacillus ferrooxidans*, which oxidizes sulfide, sulfur and iron, and *Acidithiobacillus thiooxidans*, which oxidizes sulfide and sulfur to sulfate. The processes involved in the case of microbial ore leaching can be aerobic or anaerobic. The oxygen required for this must be fed to the processes transpiring in the solids heap in sufficient amount, wherein, depending on whether the applied bacteria work aerobically or anaerobically, the supplied oxygen amount must be controlled to within a range suitable for the bacteria.

For example, known from published International Application No. WO 01/18269 A1 is a method for obtaining copper from copper sulfide minerals. In the case of this method, the mineral to be digested is slurried into a bio-leaching solution and the suspension stirred in a reactor sealed relative to the environment. Copper is dissolved out of the ore by microbiologically supported processes. By means of controlled ventilation, the slurry is fed a sufficient amount of oxygen. The control is based on an oxygen measurement within the reactor in the slurry and optionally in the gas phase.

Instead of in closed reactors, the microbial leaching can also be performed in a solids heap of piled, comminuted, hard rock ore. For this, the heap is sprayed from above with a leaching liquid, for example, with an aqueous sulfuric acid solution in a concentration of, for instance, 0.5 g/l. The microorganisms required for the process are located, in such case, within the heap on the surfaces of the hard rock ore or on their own nutrient substrate. While the leaching liquid trickles through the solids heap, microbial digestion of the difficultly soluble ore minerals occurs, so that metal ions, for example, iron or copper ions become enriched in the leaching liquid. The floor of the heap is sealed relative to the rock lying therebeneath, so that the leaching liquid enriched with metal ions can be taken off by means of channels and drains and collected. The collected leaching liquid can be sprayed back from above onto the heap. In given cases, it can earlier be subjected to an analysis, in order to test the efficiency of the metal leaching and in order, in given cases, to determine the acid consumption during the trickling of the leaching liquid through the heap. Corresponding to the ascertained acid consumption, acid can be added to the leaching liquid, before it is sprayed anew onto the heap. When the recirculated leaching liquid has become sufficiently enriched with the desired metals, the metal ions can be extracted, for example, by precipitation. The remaining, now metal ion poor, leaching liquid can, thereafter, be applied anew onto the heap. The ore leaching can last in this manner up to 150 days and achieve metal yields from the ore of up to 80%.

In order to provide sufficient oxygen for the microbial leaching process, the heap is aerated, for example, from its bottom, with oxygen rich air. In order to monitor and, in given cases, to be able to control (open or closed loop control) the aerating of the heap, a measuring of the oxygen concentration within the heap is required.

In the article, H. M. Lizama, *Copper bio-leaching behavior in an aerated heap*, Int. J. Miner. Process. 62 (2001), Pgs. 257-269, oxygen measurement within a solids heap is described, in the case of which gas samples are removed at different heights in the heap, wherein a steel tube is inserted down to desired depths of the solids heap and gas samples sucked from the different depths through the steel tube. Gas samples are fed to an oxygen gas sensor arranged outside the solids heap, and the oxygen concentrations in the gas samples measured.

Disadvantageous in such a method is, on the one hand, that it only delivers information concerning the oxygen concentration of the gas sample under the conditions reigning in the gas analyzer. No information concerning the locally (i.e. at the site of the sample taking) reigning oxygen partial pressure is provided. While, as a rule, standard conditions, such as a pressure of 1013 hPa, a standard temperature, e.g. 0° C., reign in gas analyzers, and the gas is usually dried before the measuring, there exists within the hard rock ore heap a pressure gradient resulting from the ventilation, increased temperatures resulting from the metabolism of the microorganisms and high humidity due to the leaching liquid trickling through the heap. Moreover, the sucking of the gas samples through the long steel tube can lead to delay and a "blurring" of the measurement results. The known method is, consequently, not in all cases precise enough.

SUMMARY OF THE INVENTION

It is, consequently, an object of the invention to provide a measuring arrangement, which overcomes the disadvantages of the state of the art.

This object is achieved by an arrangement for in situ measurement of at least one oxygen partial pressure within a solids heap, comprising: at least one measuring transducer arranged within the solids heap for locally registering oxygen partial pressure, wherein each measuring transducer is embodied to output a measurement signal representing oxygen partial pressure to a superordinated unit, which is arranged outside the solids heap and is embodied to receive and to process the measurement signals of each measuring transducer.

Chemical, biological processes are more dependent on the locally reigning, oxygen partial pressure than on the local oxygen concentration. As a rule, an increased oxygen partial pressure accelerates the reaction kinetics of such processes. By locally registering the oxygen partial pressure using at least one measuring transducer arranged within the solids heap, deductions can directly be made concerning the state of the chemical, biological process. Alternative measuring methods, such as those described above, in the case of which samples are removed locally from the solids heap gas and analyzed remotely from the solids heap, deliver, in contrast, no information concerning the oxygen partial pressure reigning locally within the solids heap. They are, consequently, inferior to measurements made with the assistance of the arrangement of the invention. During injection of oxygen enriched air into the solids heap by means of the ventilation system, there arises at the base of the heap a significantly positive pressure, which falls upwardly and outwardly. The oxygen partial pressure gradient resulting therefrom superimposes on an oxygen partial pressure gradient due to the chemical, biological process to form within the heap a total oxygen partial pressure profile. A precise monitoring and/or control of the bio-leaching process can, consequently, be achieved advantageously by a local oxygen partial pressure registering in the form of an in situ measurement.

Additionally to the improved accuracy, such a direct measurement is more economically and rapidly available than the above described measuring by means of a gas sensor located remotely from the sampling location.

In a preferred embodiment, the arrangement includes at least two measuring transducers arranged within the solids heap for locally registering oxygen partial pressure. The application of two or more measuring transducers for locally registering oxygen partial pressure within the solids heap permits the determining of an oxygen profile, i.e. how oxygen partial pressure is distributed within the solids heap, and permits consequently a yet more precise control of the oxygen supply by means of the ventilation.

The at least two measuring transducers can be arranged at different measuring locations situated within the solids heap. The measurement locations can lie, for example, at different depths within the solids heap and/or be arranged spaced from one another in the horizontal direction. In this way, an option is provided to determine a profile, respectively a curve, for the oxygen content within the solids heap and, correspondingly, to control ventilation of the solids heap for achieving a certain profile.

The superordinated unit can be a control unit, for example, a programmable logic controller or a process control system, which is applied also for controlling the process performed in the solids heap, for example, a microbial leaching, especially also for controlling ventilation of the solids heap. The at least one measuring transducer can be embodied to output a signal processable by the control system. If the arrangement comprises a plurality of measuring transducers, some of these measuring transducers, preferably all of the measuring transducers of the arrangement, can be embodied to output signals processable by the control system.

In another embodiment, the superordinated unit can comprise a data processing system connected with the at least one measuring transducer and arranged outside the solids heap and embodied to receive and to process the measurement signals from the at least one, respectively plurality of, measuring transducer(s). The data processing system can comprise, for example, a measurement transmitter or another computer or microcomputer. In question comes, for example, one of the Liquiline measurement transmitters of the assignee. The data processing system can also be formed of a plurality of individual modules, for example, a plurality of measurement transmitters, which can be connected for communication with one another or for communication with a control unit for the process being performed in the solids heap, for example, a microbial leaching process. The data processing system can, supplementally or alternatively, comprise a registering device or be connected with a registering device.

Serving as a control unit can be, for example, a programmable logic controller, a process control system or the like. Since the invention permits the ascertaining of the oxygen partial pressure actually reigning at the one or more measuring locations within the solids heap, especially an oxygen partial pressure profile within the solids heap, the control unit can by means of the ventilating system very precisely assure an oxygen injection optimal for the microbial leaching. This can lead to an improved extraction rate, respectively yield, from the leaching process. An improved yield permits, for example, in the case of the initially described circulatory process, in the case of which leaching liquid is applied multiple times on the solids heap, in order to enrich the leaching liquid progressively with metal ions, a lessening of the number of process cycles and therewith a shortening of the time required for the method. Along with this, energy and cost savings result from the improved control.

In an embodiment, the at least one measuring transducer can be arranged, at least partially, within a protective tube, for example, a protective tube of steel, which extends from a site on the surface of the solids heap down to the desired measuring location, where the oxygen content is to be locally measured. If the arrangement has a number of measuring transducers, these can be arranged correspondingly, at least partially, within their own protective tubes. Cable connection between the measuring transducer, respectively the measuring transducers, and the data processing system arranged outside the solids heap can extend, at least partially, through the one or more protective tubes. Alternatively, the at least one measuring transducer can be embodied very robustly, for example, using a stable housing having a protective system, e.g. a protective cage, which surrounds a sensor element of the measuring transducer, so that the measuring transducer can be buried or piled on.

One or more of the measuring transducers of the arrangement can be selected from, for example, electrochemical, especially amperometric or potentiometric, oxygen sensors. A known variant of amperometric oxygen sensors is the Clark electrode, which is known, for example, from U.S. Pat. No. 2,913,386. The Endress +Hauser sells such electrochemical measuring transducers for determining oxygen concentration, for example, under the designations, OXYMAX COS 51 and OXYMAX COS 71. A Clark electrode includes, separated by a membrane from the measured medium, here a gas present in the heap or a liquid present in the heap, an electrolyte chamber, which contains an aqueous electrolyte solution, for example, a potassium chloride solution or some other halide containing, salt solution. Immersed in the electrolyte solution are two electrodes, of which one is connected as a cathode and the other as an anode. Oxygen can diffuse from the measured medium through the membrane into the electrolyte solution and there be reduced on the cathode. The cathode current serving as measurement signal of this measuring transducer is, in such case, proportional to the oxygen partial pressure in the measured medium.

In a preferred embodiment, the at least one measuring transducer is an optical oxygen sensor, especially an oxygen sensor working according to the principle of fluorescence quenching. If a plurality of measuring transducer are provided, one, some or all of the measuring transducers can be embodied as optical oxygen sensors. Endress +Hauser sells such optical oxygen sensors, for example, under the designation OXYMAX COS 61. Such measuring transducers comprise a membrane, in which fluorescing marker molecules, for example, transition metal complexes, are contained, as well as an excitation light source, for example, one or more LEDs, as well as a photoelectric detector, for example, one or more photodiodes, which register the fluorescent radiation emitted by the marker molecules contained in the membrane. The velocity, with which the fluorescence of the marker molecules decays, is a measure for the oxygen partial pressure in the area of the membrane. Serving as measurement signal of such an optical measuring transducer is the electrical signal output by the photoelectric detector.

Such optical measuring transducers have the advantage that they can also be applied in chemically aggressive environments or in media; which contain chemical components, especially sulfur compounds, which can lead to a poisoning of an electrochemical measuring cell. The described optical measuring principle is, moreover, suitable for use in the case of changing environmental conditions, so that the measuring transducers deliver equally stable and reliable measured values in water-containing gas or when wetted by the leaching liquid. A flowing of gas or liquid on the sensitive membrane is not required for a sufficient measurement quality.

A further advantage of optical measuring transducers is the small maintenance effort required for stable operation of the measuring transducers. It is true that the membrane of a measuring transducer working according to the principle of fluorescence quenching should be replaced from time to time, the measuring transducer newly calibrated and, in given cases, adjusted. The maintenance intervals are, however, quite long, for example, in the order of magnitude of a year, so that the maintenance effort, relative to the maintenance effort for a gas analyzer or also relative to the maintenance effort for an electrochemical oxygen measuring cell, is relatively small.

Also, the capital costs for the here described arrangement with optical oxygen sensors are clearly smaller in comparison to the costs for the technology described in the above cited article.

Optical measuring transducers are distinguished supplementally also by a small electrical current requirement, especially in comparison to electrochemical measuring transducers, since they only need to be supplied with electrical current at the instant of the measuring. In contrast therewith, electrochemical measuring transducers should be supplied continuously with energy, in order to maintain the polarization. Preferably, the arrangement can, to the extent that the measuring transducers are optical measuring transducers, consequently, be embodied to work intermittently, i.e. the at least one or more measuring transducers are supplied with energy only during certain time intervals, when measured values are to be registered.

In an additional advantageous embodiment, the at least one measuring transducer can include a temperature sensor, which registers the local temperature at the measuring location, wherein the measuring transducers are embodied to output, besides the measurement signal representing oxygen partial pressure, a temperature measurement signal representing the temperature registered by the temperature sensor. If a plurality of measuring transducers are present, some or all of the measuring transducers can include temperature sensors, which register the local temperatures at the respective measuring locations, and are embodied to output, besides the measurement signal representing oxygen partial pressure, temperature measurement signals representing the temperatures registered by the temperature sensors. The temperature measurement signals can be output, for example, to the superordinated unit or to the above mentioned data processing system. Alternatively at the measuring locations, where the measuring transducers are arranged for measuring the oxygen content, additional temperature sensors can be arranged, which register the temperatures reigning at the measuring locations and are embodied to output measurement signals representing the registered temperatures. These additional temperature sensors can be connected with the superordinated unit and/or with the data processing system via cable connections, which, in case the measuring transducers for oxygen measurement are, such as above described, arranged in protective tubes, likewise extend through the protective tubes.

The data processing system can be embodied to control ventilation of the solids heap. Alternatively, the data processing system can also be embodied only for registering and additional processing and output of the measurement signals obtained from the measuring transducers and, in given cases, the temperature sensors and for output of the measurement signals or the further processed measurement signals to a control unit for control and ventilation of the solids heap. In this case, the data processing system is connected for wireless or wired communication with the control unit. The data processing system can, moreover, have a user interface for output of measured values derived from the measurement signals or for input of parameters or commands by the user.

The at least one measuring transducer and, in case present, the data processing system can be operable by means of a photovoltaic energy supply, so that the arrangement can be operated independently of the presence of an electrical current source in the vicinity of the solids heap. If the arrangement comprises a plurality of measuring transducers, preferably all measuring transducers are operated by means of the photovoltaic energy supply. Also, in this embodiment, optical measuring transducers are especially advantageous, since they, such as explained above, exhibit only a small electrical current consumption and/or can be operated intermittently, so that a small photovoltaic energy supply with a relatively small solar module (solar panel) is sufficient. Such an arrangement can especially be embodied to be transportable, i.e. mobile.

The arrangement, especially a mobile arrangement, can have, for example, a housing sealed relative to the environment, wherein the data processing system is arranged in a housing sealable relative to the environment and connected with a solar module (solar panel) on an outer wall, and wherein there is arranged in the housing an energy supply unit, which stores and/or provides to the data processing system electrical energy won by means of the solar panel. The energy supply unit can include as energy buffer an energy storer, for example, a rechargeable battery.

BRIEF DESCRIPTION OF THE DRAWINGS

The invention will now be described in greater detail based on an example of an embodiment illustrated in the appended drawing, the sole figure of which shows as follows:

FIG. 1 is a schematic representation of an arrangement for measuring oxygen partial pressure at a plurality of mutually spaced measuring locations within a solids heap.

DETAILED DISCUSSION IN CONJUNCTION WITH THE DRAWINGS

FIG. 1 shows schematically an arrangement 1 for locally measuring the oxygen partial pressure at a plurality of measuring locations 2, 3, 4, 5 in an (only schematically indicated) solids heap 6, for example, a heap of hard rock ore. The mutually spaced measurement locations 2, 3, 4, 5 are located at different depths in the solids heap 6, so that a measuring of an oxygen distribution, respectively a profile or a curve, in the solids heap 6 is possible. Arranged at each measuring location 2, 3, 4, 5 is a measuring transducer 7, which registers an oxygen partial pressure in a gas phase present at the measuring location or in a liquid present at the measuring location, for example, a leaching liquid trickling through the solids heap, and produces a measurement signal representing the current oxygen partial pressure. The measuring transducers 7 are connected via cable connections 8 with a data processing system 9, which includes in the example shown here two measurement transmitters. Of course, the data processing system can in alternative embodiments also be embodied by a single measurement transmitter or a differently embodied computer unit having one or more processors and one or more data memories.

Measuring transducers 7 are accommodated in protective tubes 10, which can be, for example, of steel, and extend from a surface of the solids heap 6 down to the measuring locations 2, 3, 4, 5. The cable connections 8 of the measuring transducers 7 with the data processing system 9 extend within the protective tubes 10 and so are protected in their sections extending through the solids heap 6 against corrosion or mechanical damage.

Data processing system 9 is arranged in a housing 11 sealable relative to the environment. Housing 11 can be embodied, for example, as a steel cabinet with a door, which in normal operation of the arrangement 1 sealedly closes the housing 11 relative to environmental influences, and which can be opened by a service person for servicing and/or maintenance of the arrangement 1. The two measurement transmitters forming the data processing system 9 have a user interface with a display and a plurality of push buttons for the read-out of measured values and for input of commands and/or parameters. Data processing system 9 is connected with a registering device 12, which records and stores over a longer period of time the measurement signals registered by the measuring transducers 7 and/or the measured values derived therefrom.

Measuring transducers 7 are embodied in the example shown here as optical oxygen sensors working according to the principle of fluorescence quenching. Each of these oxygen sensors also has a temperature sensor (not shown), which comprises, for example, a temperature dependent resistor (e.g. Pt100). The temperature sensors register the temperatures present at the respective measuring location 2, 3, 4, 5. These measuring transducers 7 are embodied to produce, besides the measurement signals representing oxygen partial pressures reigning at the measuring location 2, 3, 4, 5, supplementally, based on the temperatures registered by the temperature sensors, temperature measurement signals and to output such via the cable connections 8 to the data processing system 9.

Energy supply of the arrangement 1, especially that of the data processing system 9, the registering device 12 and the measuring transducers 7, occurs by means of a photovoltaic-system 13, which includes a solar module 14 (solar panel), and a control device 15 for producing and providing electrical energy from sunlight striking the solar module 14. The control device 15 makes the so won electrical energy available for operation of the arrangement 1. Excess energy can be stored interiorly in an energy storer and, in the case of no sunlight, for example, at night, be made available to the arrangement 1. The control device 15 and the energy storer are accommodated together with the data processing system 9 and the registering device 12 in the housing 11. The solar module 14 can be secured on an outer wall of the housing. Because of the relatively small energy requirement of the optical measuring transducers 7, it is possible to operate the installation with a relatively small solar module 14. The cabinet device shown in FIG. 1 is embodied as a portable, thus, mobile, device, so that it can be used advantageously at different locations of the solids heap 6 or successively at different solids heaps 6. In the example shown here, the cabinet is mounted on a support stand 16.

Data processing system 9 can be connected per radio or by wire with a remote control unit (not shown) for the leaching process, which, among other things, controls ventilation of the solids heap 6, and can transmit the currently registered measured values or control signals derived therefrom to the control unit. The control unit can, based on the received measured values, control (open and/or closed loop control) the ventilation of the solids heap 6. The energy supply of the measuring transducers and the data processing system 6 can, in this case, also be controlled, especially by wire, from the control unit.

In another embodiment, the data processing system can also be omitted. In this case, the measuring transducers are embodied directly to output a signal processable by the control unit, for example, a 4-20 mA signal, a HART signal, a FIELDBUS signal or the like. The measuring transducers can be connected for this directly with the control unit, for example, via wires, and can be supplied with energy directly from the control unit.

In another, more compact variant for smaller applications, a control system can be provided within the cabinet device and connected with a ventilating system for controlling the oxygen supply in the solids heap. Especially in this case, the data processing system connected with the measuring transducers can be embodied to control the process, especially the ventilation.

Besides the here described embodiments of the invention, a large number of variations and variants can come to mind. For example, the invention can be applied not only for local oxygen measurement in ore heaps, but, instead, equally in other processes, which are performed in solids heaps, such as, for example, composting or decontamination treatments.

Besides oxygen partial pressure and temperature, in the case of these and other methods, other parameters, such as pH-value, redox potential, conductivity, turbidity, respectively solids content, concentrations of certain analytes, the concentration of free acid, bacteria count, respectively cell growth, pressure or nutrient content can be registered locally, i.e. by measuring transducers arranged at one or more measuring locations distributed within the solids heap, and output to a superordinated data processing system.

The invention claimed is:

1. An arrangement for in situ measurement of at least one oxygen partial pressure within a solids heap, comprising:
   a superordinated unit; and
   at least two measuring transducers arranged within the solids heap for locally registering an oxygen partial pressure, wherein:
   each measuring transducer is embodied to output a measurement signal representing an oxygen partial pressure to said superordinated unit, which is arranged outside the solids heap and is embodied to receive and to process the measurement signals of each measuring transducer;

the at least two measuring transducers are arranged within the solids heap at measuring locations remote from one another, separated both vertically and horizontally; and said at least two measuring transducers comprise optical oxygen sensors structured to operate by fluorescence quenching to register the oxygen partial pressure.

2. The arrangement as claimed in claim 1, wherein:

said at least two measuring transducers are arranged, at least partially, each within a protective tube, which extends from a site on a surface of the solids heap down to the measuring location, at which said measuring transducer is arranged.

3. The arrangement as claimed in claim 1, wherein:

each of said at least two measuring transducers include a temperature sensor structured to, register a local temperature; and said measuring transducers are embodied to output, besides the measurement signal representing oxygen partial pressure, a temperature measurement signal representing the temperature registered by the temperature sensors.

4. The arrangement as claimed in claim 1, wherein:

said superordinated unit includes a data processing system connected with the at least two measuring transducers, arranged outside the solids heap and embodied to receive and to process the measurement signals of said at least two measuring transducers.

5. The arrangement as claimed in claim 4, wherein:

said data processing system is configured to operate on the measurement signals to generate commands for controlling ventilation of the solids heap, and/or the data processing system is in wireless or wired communication with a control unit configured to operate on an input from the data processing system to generate commands for controlling ventilation of the solids heap.

6. The arrangement as claimed in claim 4, wherein:

said at least two measuring transducers, and/or the data processing system, are powered by a photovoltaic energy supply.

7. The arrangement as claimed in claim 4, wherein:

said data processing system is arranged in a housing sealed relative to an environment and connected with a solar module secured on an outer wall of the housing; and the housing includes an energy supply unit therein, which stores and/or provides to the data processing system electrical energy generated by the solar module.

8. The arrangement as claimed in claim 4, wherein:

each measuring transducer of the arrangement and the data processing system are operable by means of a photovoltaic energy supply.

9. The arrangement as claimed in claim 1, wherein said superordinated unit includes a data processing system connected with the at least two measuring transducers, arranged outside the solids heap, and embodied to receive and to process the measurement signals of said at least two measuring transducers, and wherein said data processing system is embodied to operate on the measurement signals to control a microbial leaching process performed in the ore heap.

10. The arrangement as claimed in claim 1, wherein said superordinated unit includes a data processing system connected with the at least two measuring transducers, arranged outside the solids heap, and embodied to receive and to process the measurement signals of said at least two measuring transducers, and the superordinated unit is connected for wireless or wired communication with a control unit controlling a micribial leaching process performed in the ore heap.

11. The arrangement as claimed in claim 1, wherein the solids heap is an ore heap.

* * * * *